(12) United States Patent
Eaton et al.

(10) Patent No.: US 7,951,131 B2
(45) Date of Patent: *May 31, 2011

(54) SINUS DELIVERY OF SUSTAINED RELEASE THERAPEUTICS

(75) Inventors: Donald J. Eaton, Los Altos, CA (US); Mary L. Moran, Woodside, CA (US); Rodney A. Brenneman, San Juan Capistrano, CA (US)

(73) Assignee: Intersect ENT, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/883,079

(22) Filed: Sep. 15, 2010

(65) Prior Publication Data

US 2011/0004195 A1    Jan. 6, 2011

Related U.S. Application Data

(63) Continuation of application No. 12/258,277, filed on Oct. 24, 2008, which is a continuation of application No. 10/800,162, filed on Mar. 12, 2004, now Pat. No. 7,544,192.

(60) Provisional application No. 60/454,918, filed on Mar. 14, 2003.

(51) Int. Cl.
*A61M 31/00* (2006.01)
*A61F 13/00* (2006.01)

(52) U.S. Cl. ......... 604/506; 604/510; 604/514; 424/434

(58) Field of Classification Search ............... 604/93.01, 604/891.1, 57, 59–64, 510, 514, 506; 424/434; 606/196

See application file for complete search history.

(56) References Cited

U.S. PATENT DOCUMENTS

| | | |
|---|---|---|
| 4,580,568 A | 4/1986 | Gianturco |
| 4,737,141 A | 4/1988 | Spits |
| 4,753,636 A | 6/1988 | Free |
| 5,035,706 A | 7/1991 | Giantureo et al. |
| 5,116,311 A | 5/1992 | Löfstedt |
| 5,139,832 A | 8/1992 | Hayashi et al. |
| 5,189,110 A | 2/1993 | Ikematu et al. |
| 5,246,455 A | 9/1993 | Shikani |
| 5,342,296 A | 8/1994 | Persson et al. |

(Continued)

FOREIGN PATENT DOCUMENTS

DE    101 05 592 A1    8/2002

(Continued)

OTHER PUBLICATIONS

Final Office Action mailed on Jan. 8, 2009 for U.S. Appl. No. 10/800,162, filed Mar. 12, 2004, 5 pages.

(Continued)

*Primary Examiner* — Theodore J Stigell
*Assistant Examiner* — Catherine N Witczak
(74) *Attorney, Agent, or Firm* — Morrison & Foester LLP

(57) ABSTRACT

The invention provides biodegradable implants for treating sinusitis. The biodegradable implants have a size, shape, density, viscosity, and/or mucoadhesiveness that prevents them from being substantially cleared by the mucociliary lining of the sinuses during the intended treatment period. The biodegradable implants include a sustained release therapeutic, e.g., an antibiotic, a steroidal anti-inflammatory agent, or both. The biodegradable implants may take various forms, such as rods, pellets, beads, strips, or microparticles, and may be delivered into a sinus in various pharmaceutically acceptable carriers.

32 Claims, 2 Drawing Sheets

U.S. PATENT DOCUMENTS

| | | | |
|---|---|---|---|
| 5,443,498 | A | 8/1995 | Fontaine |
| 5,507,807 | A * | 4/1996 | Shippert ............................ 623/8 |
| 5,512,055 | A | 4/1996 | Domb et al. |
| 5,538,738 | A | 7/1996 | Ritter et al. |
| 5,664,567 | A | 9/1997 | Linder |
| 5,672,179 | A | 9/1997 | Garth et al. |
| 5,693,065 | A | 12/1997 | Rains, III |
| 5,792,100 | A | 8/1998 | Shantha |
| 5,928,190 | A | 7/1999 | Davis |
| 6,054,122 | A | 4/2000 | MacPhee et al. |
| 6,149,944 | A | 11/2000 | Jeong et al. |
| 6,190,353 | B1 | 2/2001 | Makower et al. |
| 6,195,225 | B1 | 2/2001 | Komatsu et al. |
| 6,228,111 | B1 * | 5/2001 | Tormala et al. .............. 623/1.38 |
| 6,297,227 | B1 | 10/2001 | Johnson |
| 6,302,875 | B1 | 10/2001 | Makower et al. |
| 6,543,452 | B1 | 4/2003 | Lavigne |
| 6,544,230 | B1 | 4/2003 | Flaherty et al. |
| 6,555,566 | B2 | 4/2003 | Ponikau |
| 6,565,597 | B1 | 5/2003 | Fearnot et al. |
| 6,685,648 | B2 | 2/2004 | Flaherty et al. |
| 6,715,485 | B1 | 4/2004 | Djupesland et al. |
| 6,746,426 | B1 | 6/2004 | Flaherty et al. |
| 6,749,617 | B1 | 6/2004 | Palasis et al. |
| 6,884,260 | B2 | 4/2005 | Kugler et al. |
| 6,945,992 | B2 | 9/2005 | Goodson, IV et al. |
| 6,966,923 | B2 | 11/2005 | Gittings |
| RE39,321 | E | 10/2006 | MacPhee et al. |
| 7,361,168 | B2 | 4/2008 | Makower et al. |
| 7,410,480 | B2 | 8/2008 | Muni et al. |
| 7,419,497 | B2 | 9/2008 | Muni et al. |
| 7,462,175 | B2 | 12/2008 | Chang et al. |
| 7,500,971 | B2 | 3/2009 | Chang et al. |
| 7,520,876 | B2 | 4/2009 | Ressemann et al. |
| 7,544,192 | B2 * | 6/2009 | Eaton et al. .................... 604/506 |
| 7,559,925 | B2 | 7/2009 | Goldfarb et al. |
| 7,641,644 | B2 | 1/2010 | Chang et al. |
| 7,645,272 | B2 | 1/2010 | Chang et al. |
| 7,654,997 | B2 | 2/2010 | Makower et al. |
| 7,662,141 | B2 * | 2/2010 | Eaton et al. .................... 604/506 |
| 7,662,142 | B2 * | 2/2010 | Eaton et al. .................... 604/506 |
| 7,686,798 | B2 * | 3/2010 | Eaton et al. .................... 604/506 |
| 7,691,094 | B2 * | 4/2010 | Eaton et al. .................... 604/506 |
| 7,713,255 | B2 * | 5/2010 | Eaton et al. .................... 604/506 |
| 2002/0051793 | A1 | 5/2002 | Drabick |
| 2002/0111603 | A1 * | 8/2002 | Cheikh ...................... 604/891.1 |
| 2003/0133877 | A1 | 7/2003 | Levin |
| 2003/0195459 | A1 * | 10/2003 | Shippert .......................... 604/16 |
| 2003/0203030 | A1 | 10/2003 | Ashton et al. |
| 2004/0043052 | A1 | 3/2004 | Hunter et al. |
| 2004/0064083 | A1 | 4/2004 | Becker |
| 2004/0116958 | A1 | 6/2004 | Gopferich et al. |
| 2005/0043706 | A1 | 2/2005 | Eaton et al. |
| 2005/0165347 | A1 * | 7/2005 | Bardy ............................. 604/60 |
| 2005/0203605 | A1 | 9/2005 | Dolan |
| 2005/0240147 | A1 | 10/2005 | Makower et al. |
| 2005/0245906 | A1 | 11/2005 | Makower et al. |
| 2006/0004286 | A1 | 1/2006 | Chang et al. |
| 2006/0004323 | A1 | 1/2006 | Chang et al. |
| 2006/0063973 | A1 | 3/2006 | Makower et al. |
| 2006/0095066 | A1 | 5/2006 | Chang et al. |
| 2006/0106361 | A1 | 5/2006 | Muni et al. |
| 2006/0142736 | A1 | 6/2006 | Hissink et al. |
| 2006/0162722 | A1 * | 7/2006 | Boehm et al. ............ 128/200.14 |
| 2006/0210605 | A1 | 9/2006 | Chang et al. |
| 2006/0265042 | A1 | 11/2006 | Catanese, III et al. |
| 2006/0276871 | A1 | 12/2006 | Lamson et al. |
| 2007/0005094 | A1 | 1/2007 | Eaton et al. |
| 2007/0129751 | A1 | 6/2007 | Muni et al. |
| 2007/0135789 | A1 | 6/2007 | Chang et al. |
| 2007/0167682 | A1 | 7/2007 | Goldfarb et al. |
| 2007/0191922 | A1 | 8/2007 | Hartley |
| 2007/0208252 | A1 | 9/2007 | Makower |
| 2007/0208301 | A1 | 9/2007 | Evard et al. |
| 2007/0249896 | A1 | 10/2007 | Goldfarb et al. |
| 2007/0269385 | A1 | 11/2007 | Yun et al. |
| 2007/0282305 | A1 | 12/2007 | Goldfarb et al. |
| 2007/0293726 | A1 | 12/2007 | Goldfarb et al. |
| 2007/0293727 | A1 | 12/2007 | Goldfarb et al. |
| 2007/0293946 | A1 | 12/2007 | Gonzales et al. |
| 2008/0015540 | A1 | 1/2008 | Muni et al. |
| 2008/0058295 | A1 | 3/2008 | Chaudry |
| 2008/0058296 | A1 | 3/2008 | Chaudry |
| 2008/0069858 | A1 | 3/2008 | Weber |
| 2008/0077230 | A1 | 3/2008 | Heaney et al. |
| 2008/0082162 | A1 | 4/2008 | Boismier et al. |
| 2008/0085293 | A1 | 4/2008 | Yang |
| 2008/0089952 | A1 | 4/2008 | Hunter et al. |
| 2008/0097154 | A1 | 4/2008 | Makower et al. |
| 2008/0097239 | A1 | 4/2008 | Chang et al. |
| 2008/0097295 | A1 | 4/2008 | Makower et al. |
| 2008/0097400 | A1 | 4/2008 | Chang et al. |
| 2008/0097514 | A1 | 4/2008 | Chang et al. |
| 2008/0097515 | A1 | 4/2008 | Chang et al. |
| 2008/0097516 | A1 | 4/2008 | Chang et al. |
| 2008/0097581 | A1 | 4/2008 | Shanley |
| 2008/0103361 | A1 | 5/2008 | Makower et al. |
| 2008/0103521 | A1 | 5/2008 | Makower et al. |
| 2008/0113000 | A1 | 5/2008 | Hunter et al. |
| 2008/0119693 | A1 | 5/2008 | Makower et al. |
| 2008/0125626 | A1 | 5/2008 | Chang et al. |
| 2008/0125720 | A1 | 5/2008 | Kim et al. |
| 2008/0132938 | A1 | 6/2008 | Chang et al. |
| 2008/0145514 | A1 | 6/2008 | Hunter et al. |
| 2008/0154237 | A1 | 6/2008 | Chang et al. |
| 2008/0154250 | A1 | 6/2008 | Makower et al. |
| 2008/0183128 | A1 | 7/2008 | Morriss et al. |
| 2008/0195041 | A1 | 8/2008 | Goldfarb et al. |
| 2008/0228085 | A1 | 9/2008 | Jenkins et al. |
| 2008/0234720 | A1 | 9/2008 | Chang et al. |
| 2008/0243140 | A1 | 10/2008 | Gopferich et al. |
| 2008/0262468 | A1 | 10/2008 | Clifford et al. |
| 2008/0262505 | A1 | 10/2008 | Shahoian |
| 2008/0262508 | A1 | 10/2008 | Clifford et al. |
| 2008/0262509 | A1 | 10/2008 | Clifford et al. |
| 2008/0262510 | A1 | 10/2008 | Clifford |
| 2008/0275483 | A1 | 11/2008 | Makower et al. |
| 2008/0281156 | A1 | 11/2008 | Makower et al. |
| 2009/0017090 | A1 | 1/2009 | Arensdorf et al. |
| 2009/0047326 | A1 | 2/2009 | Eaton et al. |
| 2009/0047327 | A1 | 2/2009 | Eaton et al. |
| 2009/0093823 | A1 | 4/2009 | Chang et al. |
| 2009/0156980 | A1 | 6/2009 | Eaton et al. |
| 2009/0177272 | A1 | 7/2009 | Abbate et al. |
| 2009/0187098 | A1 | 7/2009 | Makower et al. |
| 2009/0192488 | A1 | 7/2009 | Eaton et al. |
| 2009/0192489 | A1 | 7/2009 | Eaton et al. |
| 2009/0192490 | A1 | 7/2009 | Eaton et al. |
| 2009/0192491 | A1 | 7/2009 | Eaton et al. |
| 2009/0192492 | A1 | 7/2009 | Eaton et al. |
| 2009/0198179 | A1 | 8/2009 | Abbate et al. |
| 2009/0198216 | A1 | 8/2009 | Muni et al. |
| 2009/0220571 | A1 | 9/2009 | Eaton et al. |
| 2009/0227945 | A1 | 9/2009 | Eaton et al. |
| 2009/0238859 | A1 | 9/2009 | Eaton et al. |
| 2009/0306624 | A1 | 12/2009 | Arensdorf et al. |
| 2010/0043197 | A1 | 2/2010 | Abbate et al. |
| 2011/0004192 | A1 | 1/2011 | Eaton et al. |
| 2011/0004193 | A1 | 1/2011 | Eaton et al. |
| 2011/0004194 | A1 | 1/2011 | Eaton et al. |
| 2011/0004196 | A1 | 1/2011 | Eaton et al. |

FOREIGN PATENT DOCUMENTS

| | | |
|---|---|---|
| JP | 2-500521 A | 2/1990 |
| JP | 6-506672 A | 7/1994 |
| JP | 2000-507630 A | 6/2000 |
| JP | 2001-506144 A | 5/2001 |
| JP | 2001-520188 A | 10/2001 |
| WO | WO-89/00839 A1 | 2/1989 |
| WO | WO-97/36949 A1 | 10/1997 |
| WO | WO-99/20261 A2 | 4/1999 |
| WO | WO-99/20261 A3 | 4/1999 |
| WO | WO-01/02024 A1 | 1/2001 |
| WO | WO-01/02024 C1 | 1/2001 |
| WO | WO-01/26658 A2 | 4/2001 |
| WO | WO-01/26658 A3 | 4/2001 |
| WO | WO-2004/082525 A2 | 9/2004 |

| WO | WO-2004/082525 A3 | 9/2004 |
| WO | WO-2006/020180 A2 | 2/2006 |
| WO | WO-2006/020180 A3 | 2/2006 |
| WO | WO-2006/107957 A2 | 10/2006 |
| WO | WO-2006/107957 A3 | 10/2006 |
| WO | WO-2007/134215 A2 | 11/2007 |
| WO | WO-2007/134215 A3 | 11/2007 |
| WO | WO-2008/008389 A2 | 1/2008 |
| WO | WO-2008/008389 A3 | 1/2008 |
| WO | WO-2009/079418 A2 | 6/2009 |
| WO | WO-2009/079418 A3 | 6/2009 |
| WO | WO-2010/014834 A1 | 2/2010 |

OTHER PUBLICATIONS

Final Office Action mailed on Jul. 22, 2009, for U.S. Appl. No. 11/398,342, filed Apr. 4, 2006, 8 pages.
Final Office Action mailed on Jul. 8, 2010, for U.S. Appl. No. 11/398,342, filed Apr. 4, 2006, 7 pages.
Hosemann, W. et al. (Mar. 2003, e-pub. Oct. 10, 2002). "Innovative Frontal Sinus Stent Acting as a Local Drug-Releasing System," *Eur. Arch. Otorhinolarynol.* 260:131-134.
International Search Report mailed Feb. 24, 2006 for PCT Application No. PCT/US04/07828 filed Mar. 12, 2004, 2 pages.
Lapchenko, A.S. et al. (Jun. 1996). "Polyphosphazene Prosthesis of the Frontonasal Bypass in Surgical Treatment of Acute and Chronic Inflammation of the Frontal Sinuses," *Vestnik Otorinolarinologii,* two pages.
Lavigne, F. et al. (May 2002). "Intrasinus Administration of Topical Budesonide to Allergic Patients With Chronic Rhinosinusitis Following Surgery," *The Laryngoscope* 112, seven pages.
Min, Y-G. et al. (1995). "Application of Polylactic Acid Polymer in the Treatment of Acute Maxillary Sinusitis in Rabbits," *Acta Otolaryngol.* 115:548-552.
Min, Y-G. et al. (Aug. 1995). "Mucociliary Activity and Histopathology of Sinus Mucosa in Experimental Maxillary Sinusitis: A Comparison of Systemic Administration of Antibiotic and Antibiotic Delivery by Polylactic Acid Polymer," *The Laryngoscope* 105:835-842.
Non-Final Office Action mailed on Jun. 6, 2008, for U.S. Appl. No. 10/800,162, filed Mar. 12, 2004, 5 pages.
Non-Final Office Action mailed on Nov. 25, 2008, for U.S. Appl. No. 11/398,342, filed Apr. 4, 2006, 10 pages.
Non-Final Office Action mailed on Sep. 22, 2009, for U.S. Appl. No. 12/419,927, filed Apr. 7, 2009, 4 pages.
Non-Final Office Action mailed on Sep. 22, 2009, for U.S. Appl. No. 12/419,943, filed Apr. 7, 2009, 5 pages.
Non-Final Office Action mailed on Sep. 22, 2009, for U.S. Appl. No. 12/419,930, filed Apr. 7, 2007, 4 pages.
Non-Final Office Action mailed on Sep. 22, 2009, for U.S. Appl. No. 12/419,937, filed Apr. 7, 2009, 4 pages.
Non-Final Office Action mailed on Sep. 22, 2009, for U.S. Appl. No. 12/419,925, filed Apr. 7, 2009, 4 pages.
Non-Final Office Action mailed on Nov. 13, 2009, for U.S. Appl. No. 11/398,342, filed Apr. 4, 2006, 9 pages.
Non-Final Office Action mailed on Jul. 1, 2010, for U.S. Appl. No. 12/479,794, filed Jun. 6, 2009, 5 pages.
Non-Final Office Action mailed on Nov. 12, 2010, for U.S. Appl. No. 11/398,342, filed Apr. 4, 2006, 8 pages.
Non-Final Office Action mailed on Nov. 23, 2010, for U.S. Appl. No. 12/258,277, filed Oct. 24, 2008, 9 pages.
Non-Final Office Action mailed on Nov. 23, 2010, for U.S. Appl. No. 12/258,282, filed Oct. 24, 2008, 7 pages.
Non-Final Office Action mailed on Nov. 24, 2010, for U.S. Appl. No. 12/883,090, filed Sep. 15, 2010, 7 pages.
Non-Final Office Action mailed on Nov. 24, 2010, for U.S. Appl. No. 12/883,056, filed Sep. 15, 2010, 7 pages.
Notice of Allowance mailed on Dec. 23, 2009, for U.S. Appl. No. 12/419,925, filed Apr. 7, 2009, 2 pages.
Notice of Allowance mailed on Dec. 23, 2009, for U.S. Appl. No. 12/419,943, filed Apr. 7, 2009, 2 pages.
Notice of Allowance mailed on Dec. 24, 2009, for U.S. Appl. No. 12/419,927, filed Apr. 7, 2009, 2 pages.
Notice of Allowance mailed on Jan. 19, 2010, for U.S. Appl. No. 12/419,930, filed Apr. 7, 2009, 2 pages.
Notice of Allowance mailed on Feb. 2, 2010, for U.S. Appl. No. 12/419,937, filed Apr. 7, 2009, 2 pages.
Nuutinen, J-P. et al. (2002). "Mechanical Properties and in vitro Degradation of Bioresorbable Knitted Stents," *J. Biomater. Sci. Polymer Edn.* 13(12):1313-1323.
Nuutinen, J-P. et al. (2003). "Theoretical and Experimental Evaluation of the Radial Force of Self-Expanding Braided Bioabsorbable Stents," *J. Biomater. Sci. Polymer Edn.* 14(7):677-687.
Piskunov, S.Z. et al. (May-Jun. 1989). "Application of Drugs Based on Polymers in the Treatment of Acute and Chronic Maxillary Sinusitis," *Vestnik Otorinolaringologii* (3)33-35.
Piskunov, S. et al. (1993). "The Prolongation of Drug Action in the Treatment of Diseases of the Nose and Paranasal Sinuses," *Rhinology* 31:33-36.
Roumestan, C. et al. (2003). "Fluticasone Propionate and Mometasone Furoate Have Equivalent Transcriptional Potencies," *Clinical and Experimental Allergy* 33: 895-901.
Shikani, A.H. (Aug. 1996). "Use of Antibiotics for Expansion of the Merocel® Packing Following Endoscopic Sinus Surgery," *ENT Journal* 75(8):524-528.
Supplementary European Search Report mailed on Nov. 9, 2010, for EP Patent Application No. 04720509.1, filed on Mar. 12, 2004, 3 pages. (1.44).
Thierry, B. et al. (Nov./Dec. 2003, e-pub. Oct. 7, 2003). "Bioactive Coatings of Endovascular Stents Based on Polyelectrolyte Multilayers," *Biomacromolecules* 4(6):1564-1571.
U.S. Appl. No. 12/883,059, filed Sep. 15, 2010, by Eaton et al.

\* cited by examiner

SINUS DELIVERY OF SUSTAINED RELEASE THERAPEUTICS

RELATED APPLICATIONS

This application is a continuation of U.S. application Ser. No. 12/258,277, filed on Oct. 24, 2008; which is a continuation of U.S. application Ser. No. 10/800,162, filed on Mar. 12, 2004, now U.S. Pat. No. 7,544,192; which claims priority from U.S. Provisional Application Ser. No. 60/454,918, filed Mar. 14, 2003. Each of which are hereby incorporated by reference in their entirety.

FIELD OF THE INVENTION

This invention relates to biodegradable implants and methods for placing one or more of these implants into a paranasal sinus. The implants provide local sustained release of a therapeutic agent for the prophylaxis or treatment of sinusitis. Included in the description are implants delivered in such various forms as pellets, rods, strips, and microparticles.

BACKGROUND OF THE INVENTION

The paranasal sinuses are air-filled cavities within the facial skeleton. Each paranasal sinus is contiguous with a nasal cavity and drains into the nose through a sinus ostium. Although other factors may be involved, the development of sinusitis (inflammation of the mucosal lining of the sinuses) is most often attributed to blockage of one or more of these sinus ostia, followed by mucostasis and microbial overgrowth in the sinus cavity. Ostial blockage may stem from predisposing anatomical factors, or inflammation and edema of the mucous lining in the area of the ostia, arising from such etiologies as viral or bacterial upper respiratory infection or chronic allergic processes.

Traditionally, sinusitis has been medically managed by the oral administration of antibiotics and steroids. However, penetration of these systemically delivered agents into the sinus mucosa is limited due to poor blood flow to the sinuses. Therapeutic agents contained in aqueous solutions, creams, or gels, for topical application in the nose have also been formulated, but usually never travel far enough into the nose to reach the sinuses, are blocked from entering the sinuses due to obstructed ostia, or have such short contact with the sinus mucosa that absorption of the agent is low. For similar reasons, nasally inhaled steroid and anti-infective aerosols that have been developed to treat sinusitis are equally ineffective.

The delivery of ampicillin from a poly(lactic-co-glycolic) acid (PLGA) film to increase residence time of the antibiotic in rabbit sinuses has been investigated for the treatment of sinusitis (Min et al. Mucociliary Activity and Histopathology of Sinus Mucosa in Experimental Maxillary Sinusitis: A Comparison of Systemic Administration of Antibiotic and Antibiotic Delivery by Polylactic Acid Polymer. *Laryngoscope* 105:835-342 (1995) and Min et al. Application of Polylactic Acid Polymer in the Treatment of Acute Maxillary Sinusitis in Rabbits. *Acta Otolaryngol* 115:548-552 (1995)). Although clinical signs of sinusitis improved, the procedure for placing the film required that a hole be drilled through the anterior wall of the maxillary sinus.

Consequently, a biodegradable implant for administering a sustained release therapeutic agent to the paranasal sinuses for a prolonged time period without being substantially cleared by the mucociliary lining of the sinuses, and methods for delivering the implant in a minimally invasive fashion may provide significant medical benefit for patients afflicted with sinusitis.

SUMMARY OF THE INVENTION

The present invention is a biodegradable implant for treating sinusitis that includes a sustained release therapeutic agent dispersed within a biodegradable matrix, and which has at least one characteristic that substantially prevents clearance of the implant from the sinus by its mucociliary layer during the intended treatment period after delivery of the implant into the sinus. Characteristics such as size, shape, density, viscosity, mucoadhesiveness, or a combination thereof may be altered to substantially prevent this clearance.

The biodegradable implant may include various therapeutic agents, including, but not limited to, anti-infective agents, anti-inflammatory agents, and combinations thereof. Examples of anti-infective agents include antibacterial agents, antifungal agents, antiviral agents, and antiseptics. The anti-inflammatory agent may be a nonsteroidal anti-inflammatory agent or a steroidal anti-inflammatory agent. In a preferred variation, steroidal anti-inflammatory agents are used.

The matrix of the implant may be made from any biodegradable and biocompatible polymer, including such polymers as mucoadhesive polymers, poly(ortho esters), and poly(lactic-co-glycolic)acid (PLGA) copolymer. The biodegradable polymer matrix may also be formed as a rod, pellet, bead, strip, or microparticle, and placed in a pharmaceutically acceptable carrier if desired. When the biodegradable implant is a microparticle, usually a plurality of microparticles are delivered into the sinus to treat sinusitis. The microparticles may or may not be porous, and may have an average diameter of between about 0.1-500 µm, between about 0.1-100 µm, between about 0.1-50 µm, or between about 0.1-10 µm. In some instances, the form of the biodegradable implant may change after delivery into the sinus. For example, a poly(ortho ester) implant in the form of a strip having a series of predetermined fracture lines or zones may fracture into a plurality of smaller segments as it degrades along the fracture lines in the sinus.

The biodegradable implant may deliver a sustained release therapeutic agent over at least about one week, over at least about two weeks, over at least about three weeks, over at least about four weeks, over at least about six weeks, over at least about two months, or over at least about three months. In a preferred variation, the sustained release therapeutic agent is delivered into the sinus over about three weeks.

The biodegradable implants may be delivered into a sinus using devices of various designs, but at least which include a pusher and a conduit, e.g., a catheter, needle, or angiocatheter. For example, the pusher and/or conduit may be made such that they are variably stiff along their lengths. In addition, the opening in the conduit through which the implant is delivered may be positioned in the conduit side wall or at the tip. Furthermore, the distal portion of the conduit may be angulated to facilitate access of the sinus ostium if indicated. In one variation, the distal portion is malleable such that the physician may angulate the conduit themselves just prior to accessing the sinus ostium.

The biodegradable implants and devices for their deployment may be used in a system for treating sinusitis. In general, the system works by first placing the conduit having one or more implants within its lumen either through a sinus ostium or a sinus wall. A pusher within the lumen of the conduit is then distally advanced to slidably engage the implant(s) and move it through an opening in the distal portion of the conduit into the sinus. The opening may be in the conduit side wall or tip. Usually, the conduit will be preloaded with one or more implants. In some instances, a tool for visualizing the sinus ostium or sinus wall is desired. Examples of such tools include endoscopes and computed tomography (CT) scanners.

The biodegradable implants may also be used for reducing inflammation from a sinus procedure. These implants would also include a sustained release therapeutic agent dispersed within a biodegradable matrix and have at least one characteristic that substantially prevents clearance of the implants from a sinus during a treatment period after delivery of the implant into the sinus. The treatment period may be of any duration which the physician deems is suitable to reduce the inflammation.

BRIEF DESCRIPTION OF THE DRAWINGS

In FIG. 1A, the biodegradable implant is delivered through a side opening in the conduit. In FIG. 1B, the biodegradable implant is delivered through the tip of the conduit.

DETAILED DESCRIPTION OF THE INVENTION

Figure 1A:
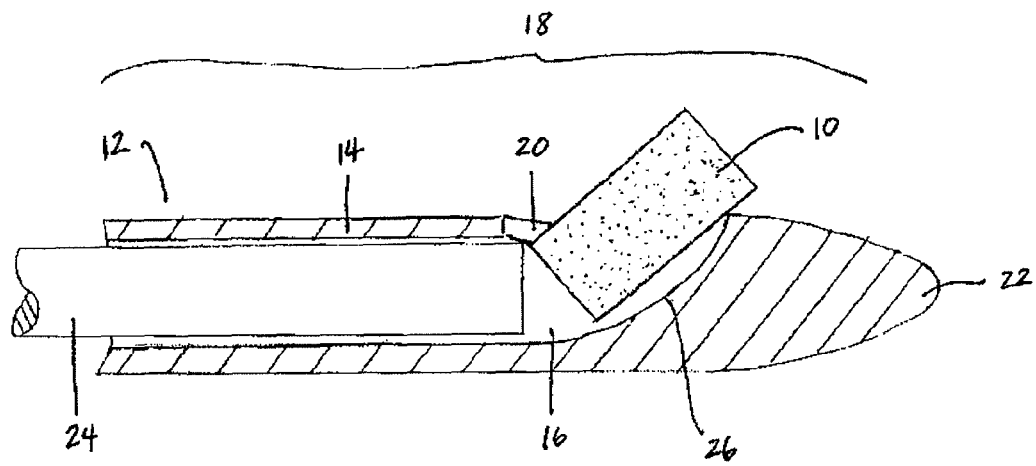
FIGS. 1A-1B are cross-sectional views of the distal portion of an implant delivery device.

The biodegradable implants of this invention may take various forms, but are generally designed to have a size and shape appropriate for the intended method of delivery, e.g., through the sinus ostium or by puncture through a sinus wall, and a density, viscosity, and/or mucoadhesiveness such that the implant is not substantially cleared from the sinus over the duration of treatment. Once within the sinus, the implant releases a therapeutic agent over a prolonged time period, for example, over at least one week, over at least two weeks, over at least three weeks, or over at least four weeks or more, to treat sinusitis.

Definitions

For purposes of this description, we use the following terms as defined in this section, unless the context of the word indicates a different meaning.

By "sinus" it is meant all sinuses, i.e., the maxillary, ethmoid, frontal, and sphenoidal sinuses.

By "subject" it is meant mammalian subjects, preferably humans. Mammals include, but are not limited to, primates, farm animals, sport animals, cats, dogs, rabbits, mice, and rats.

As used herein, the term "treat", "treating", or "treatment" refers to the resolution, reduction, or prevention of sinusitis or the sequelae of sinusitis.

As used herein, the term "therapeutic agent", "active agent", and "drug" are used interchangeably and refer to any substance used to treat sinusitis.

By "therapeutic amount" it is meant a concentration of therapeutic agent that has been locally delivered to a sinus that is appropriate to safely treat sinusitis.

Biodegradable Implants

The implants of this invention generally include a therapeutic agent dispersed within a biodegradable polymer. The therapeutic agent may be homogeneously or inhomogeneously dispersed throughout the implant. Implant compositions may vary, depending, for example, on the particular therapeutic agent employed, duration of desired drug release, type of sinusitis being treated, and medical history of the patient. However, in all instances, the biodegradable implant is formulated for sustained release of the therapeutic agent.

Therapeutic Agents

The therapeutic agents that may be used in the biodegradable implants include, but are not limited to, anti-infective agents, anti-inflammatory agents, or a combination thereof. Anti-infective agents generally include antibacterial agents, antifungal agents, antiviral agents, and antiseptics. Anti-inflammatory agents generally include steroidal and nonsteroidal anti-inflammatory agents.

Examples of antibacterial agents that may be incorporated in the biodegradable implants include aminoglycosides, amphenicols, ansamycins, β-lactams, lincosamides, macrolides, nitrofurans, quinolones, sulfonamides, sulfones, tetracyclines, and any of their derivatives. In one variation, β-lactams are the preferred antibacterial agents.

β-lactams that may be included in the implants include carbacephems, carbapenems, cephalosporins, cephamycins, monobactams, oxacephems, penicillins, and any of their derivatives. In one variation, penicillins (and their corresponding salts) are the preferred β-lactams.

The penicillins that may be used in the biodegradable implants include amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin. In one variation, amoxicillin may be included in the biodegradable implant. In another variation, the biodegradable implant includes ampicllin. Penicillins combined with clavulanic acid such as Augmentin® (amoxicillin and clavulanic acid) may also be used.

Examples of antifungal agents that may be used in the biodegradable implants include allylamines, imidazoles, polyenes, thiocarbamates, triazoles, and any of their derivatives. In one variation, imidazoles are the preferred antifungal agents.

Typically, if inclusion of an anti-inflammatory agent is desired, a steroidal anti-inflammatory agent, e.g., a corticosteroid, is employed. Examples of steroidal anti-inflammatory agents that may be used in the implants include 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives. In one variation, budesonide is included in the implant as the steroidal anti-inflammatory agent. In another variation, the steroidal anti-inflammatory agent may be mometasone furoate. In yet another variation, the steroidal anti-inflammatory agent may be beclomethasone.

The therapeutic agent may constitute from about 5% to about 90%, about 15% to about 75%, or about 30% to about 60% by weight of the implant. The amount of therapeutic agent used will usually depend on factors such as the particular agent incorporated, the suspected etiology of the sinusitis, and the severity of clinical symptoms, but in all instances will usually be an amount that is therapeutic upon delivery into a sinus. Ancillary agents such as topical decongestants may also be included.

Polymer Matrix

Selection of the biodegradable polymer matrix to be employed will vary depending on the residence time and release kinetics desired, method of implant delivery, particular therapeutic agent used, and the like. An exemplary list of biodegradable polymers that may be used are described in Heller, *Biodegradable Polymers in Controlled Drug Delivery*, In: "CRC Critical Reviews in Therapeutic Drug Carrier Systems", Vol. 1. CRC Press, Boca Raton, Fla. (1987). In all instances, the polymer matrix when degraded results in physiologically acceptable degradation products. The biodegradable polymer matrix may constitute at least about 10%, at least about 20%, at least about 30%, at least about 40%, at least about 50%, at least about 60%, at least about 70%, at least about 80%, at least about 90%, or at least about 95% by weight of the implant.

In one variation, adhesiveness of the polymer matrix to the sinus mucosa is particularly desired. Mucoadhesive polymers are typically hydrophilic, and upon moistening, swell and become adhesive. Examples of mucoadhesive polymers that may be employed in the biodegradable implants include homopolymers of acrylic acid monomers such as polyacrylic acid and any of its pharmaceutically acceptable salts; copolymers of acrylic acid and methacrylic acid, styrene, or vinyl ethers; vinyl polymers such as polyhydroxyethyl acrylate, polyhydroxyethyl methacrylate, polyvinyl alcohol, and polyvinyl pyrrolidone; cellulosic derivatives such as methyl cellulose, ethyl cellulose, hydroxyethyl cellulose, hydroxypropyl cellulose, hydroxypropylmethyl cellulose, and carboxymethyl cellulose; polysaccharides such as alginic acid, sodium alginate, and tragacanth gum; collagen; gelatin; and any combination thereof.

In another variation, the biodegradable matrix is made from an orthoester, alone or in combination with other monomers. In a preferred variation, a poly(ortho ester) is used to constitute the polymer matrix.

In yet a further variation, polymers of hydroxyaliphatic carboxylic acids, either homo- or copolymers, are used to form the matrix. For example, polyesters including homo- or copolymers of D-lactic acid, L-lactic acid, racemic lactic acid, glycolic acid, caprolactone, and combinations thereof may be used. Copolymers of glycolic and lactic acid are of particular interest, where the rate of biodegradation is controlled by the ratio of glycolic to lactic acid. The percent of each monomer in poly(lactic-co-glycolic)acid (PLGA) copolymer may be 0-100%, about 20-80%, about 30-70%, or about 40-60%. In a preferred variation, a 50/50 PLGA copolymer is used.

In one variation, PLGA may be combined with budesonide to form the biodegradable sinus implant. In another variation, PLGA may be combined with mometasone furoate. If inclusion of an antibacterial agent is desired in the PLGA matrix, alone or in combination with a steroidal anti-inflammatory agent, Augmentin® may be used. If first-line antimicrobial therapy fails, or for penicillin allergy, a cephalosporin such as ciprofloxacin or macrolide such as erythromycin may be used in the PLGA matrix.

The biodegradable implants may be solid or semisolid and take a variety of suitable forms, such as rods or approximately spherical or rectangular pellets, beads, strips, or microparticles, so long as their size and shape is compatible with the selected sinus of implantation, and so long as the implants exhibit the desired release kinetics and deliver an amount of drug therapeutic for the intended type of sinusitis. In one variation, the implant is a rod having a length of about 1 mm to about 10 mm and a diameter of about 0.05 mm to about 5 mm. In another variation, the implant is a rod having a length of about 4 mm and a diameter of about 2 mm. In yet a further variation, the implant is a microparticle. When treating sinusitis, a plurality of these microparticles with or without a carrier are delivered into the sinus. The microparticles may or may not be porous, and may have an average diameter of between about 0.1-500 µm, between about 0.1-100 µm, between about 0.1-50 µm, between about 0.1-10 µm, between about 0.1-1 µm, or between about 0.1-0.5 µm.

Also important is that the implant remain in the sinus during the intended period of drug delivery. The sinuses are lined with a ciliated epithelium and a layer of mucus. The cilia beat continuously, causing the mucous layer to slowly flow out of the sinus toward the pharynx. Accordingly, in order to effectively treat sinusitis with an implant, the implant must typically remain in the sinus long enough to deliver a drug in a therapeutic amount. The biodegradable implants of this invention have a mucoadhesiveness, size, shape, viscosity, and/or density that allows a substantial amount of the implant to remain in the sinus during the intended period of drug delivery.

Furthermore, the implant may be of a design that allows it to take a form that is different after it is delivered into the sinus from that before delivery. For instance, an implant delivered into the sinus as a rod or strip having a series of predetermined fracture lines or zones may fracture into a plurality of smaller segments as it degrades along the fracture lines.

Additional Agents

The implants of this invention may further include components such as preservatives, buffers, binders, disintegrants, lubricants, and any other excipients necessary to maintain the structure and/or function of the implants. Furthermore, the implants may be placed in a pharmaceutically acceptable carrier, e.g., when the implants are microparticles, to form a suspension such as a semi-solid gel. Common gel bases include, but are not limited to, carbomer, liquid paraffin, water, glycerol, propylene glycol, hyaluronic acid or sodium hyaluronate, or a combination thereof. The types of gels that may be formed include, e.g., inorganic and organic gels, hydrogels, or organogels.

In addition to microparticle density, the viscosity of the gel may be adjusted to a level that allows delivery into the sinus and prevents substantial clearance of the microparticles (implants) from the sinus. The gel may also be prepared in adhesive form (using adhesive polymers such as polyacrylic acid, sodium carboxymethyl cellulose, or polyvinylpyrrolidone) to increase the contact time of the therapeutic agent with the sinus mucosa.

Release Kinetics

In general, the implants of this invention are formulated with particles of a therapeutic agent dispersed within a biodegradable polymer matrix, and formulated to provide sustained-release of the therapeutic agent. If made from a non-swellable polymer, e.g., PLGA or poly(ortho ester), release of the active agent from the matrix is probably achieved by erosion of the biodegradable polymer matrix and by diffusion of the particulate therapeutic agent into the mucous layer of the sinus. Factors that may influence the release kinetics include such characteristics as the size of the drug particles, the solubility of the drug, the ratio of drug to polymer(s), the method of implant manufacture, the implant surface area exposed, and the erosion rate of the matrix polymer(s). In the case of polymer swelling, as seen with hydrogels, a therapeutic agent is released as liquid diffuses through exposed pathways in the implant.

The therapeutic agent may be released from the implant over a prolonged time period including, but not limited to, at least about one week, at least about two weeks, at least about three weeks, at least about four weeks, at least about 6 weeks, at least about two months, or at least about three months. In one variation, the therapeutic agent is released over about two weeks to about four weeks.

Delivery Device

The biodegradable implants may be placed into the sinus using various implant delivery devices. The device generally includes a conduit, e.g., a catheter, having an elongate pusher within its lumen. The conduit and pusher may be flexible or rigid, or may be designed to have varying degrees of stiffness along its length, e.g., the distal portion of the conduit may be stiffer than the proximal portion. In addition, the distal portion of the conduit may be variously angulated to facilitate positioning and advancement of the conduit through the sinus ostium. For example, the distal portion may be angulated from about 0° to about 175°, from about 0° to about 135°, or from about 0° to about 90°.

The conduit may be made from any biocompatible material including, but not limited to, stainless steel and any of its alloys; titanium alloys, e.g., nickel-titanium alloys; polymers, e.g., polyethylene and copolymers thereof, polyethylene terephthalate or copolymers thereof, nylon, silicone, polyurethanes, fluoropolymers, poly (vinylchloride), and combinations thereof, depending on the amount of flexibility or stiffness desired. The pusher may be made from similar materials.

Usually, the device will be preloaded with a single implant within the lumen of the conduit, but more than one implant may be preloaded if desired. Once access through a sinus ostium has been obtained with the conduit, the pusher slidably engages the implant and is advanced until the implant exits the catheter into the sinus. An endoscope may also be used while positioning the conduit to aid with visualization of the ostium.

In certain cases, e.g., when ostia are closed or difficult to access, implant placement into one or more sinuses may be completed through the sinus wall using a sharp-tipped conduit, e.g., a needle, trocar, or angiocatheter, with or without visualization using computer image-guided technology or endoscopy. Once the appropriate access point for the sinus has been determined, force is applied to the sharp-tipped conduit so that it punctures the sinus wall. Advancement of a pusher through the conduit lumen then deposits an implant into the sinus.

Figure 1B:
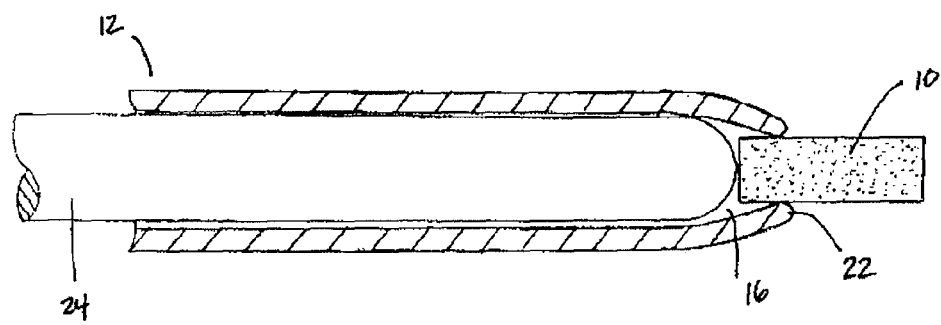

FIGS. 1A-1B show examples of single implant delivery devices. The devices include an implant 10, a conduit 12 having a side wall 14, a lumen 16, a distal portion 18, an opening 20 in the distal portion 18, a tip 22, and a pusher 24. In FIG. 1A, the conduit 12 includes a ramp 26 and an opening 20 positioned in the side wall 14. If delivering a solid implant, the opening will usually be approximately twice the diameter of the implant. The pusher 24 is advanced distally within the lumen 16 to slidably engage the implant 10 and move it up the ramp 26 through the side wall 14 into the sinus. In FIG. 1B, the opening 20 is positioned at the tip 22 of the conduit 12, and pusher 24 is advanced distally within the lumen 16 to slidably engage the implant 10 and move it through the tip 22. Although the conduit tips are shown to be blunt in the Figures, they may also be sharp and/or beveled, usually depending on the implant delivery method.

Figure 2A:
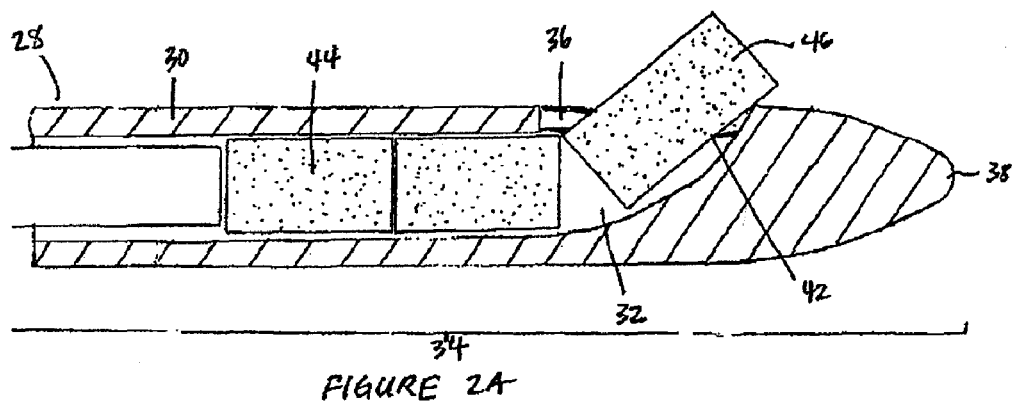
FIG. 2A is a cross-sectional view of a distal portion of a multiple implant delivery device.

FIG. 2A shows a device that delivers multiple implants. The device is similar to the single implant delivery device having a conduit 28 with a side wall 30, a lumen 32, a distal portion 34, an opening 36 in the distal portion 34, a tip 38, a pusher 40, and a ramp 42. Pusher 40 is distally advanced a preset distance to slidably engage the most proximal implant 44 within lumen 32. The pusher 40 is then further distally advanced a preset distance, e.g., a distance approximately equal to the length of one implant, to move the most distal implant 46 through opening 36 into the sinus.

Figure 2B:
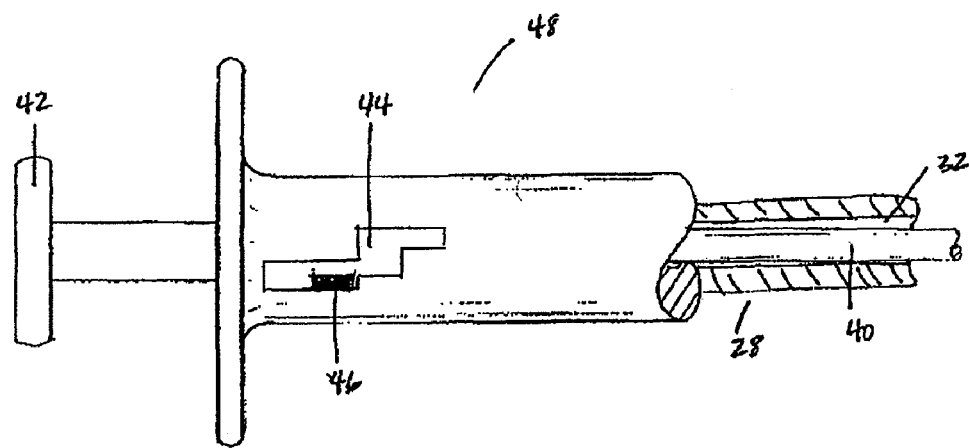
FIG. 2B is a cross-sectional view of a handle that may be coupled to the distal portion of the multiple implant delivery device shown in FIG. 2A.

A handle 48, as shown in FIG. 2B, may be coupled to conduit 28 such that the handle lumen forms a continuous lumen with the lumen 32 of the conduit 28. The pusher 40 can then slide through this continuous lumen. The handle 48 further includes an injector 42, adjacent to and longitudinally aligned with the pusher 40, and a stepped slot 44 with various positions "O", "A", "B", and "C". Initially, when the injector 42 is pressed, the pusher 40 is distally advanced, and a key 46 coupled to the injector 42 moves the pusher 40 between positions "O" and "A". The distance between positions "O" and "A" is approximately equal to the length of the dispensed implant. Pusher 40 may then be rotated to move the key 46 from position "A" to position "B" in the stepped slot 44. Pressing the injector 42 again then moves the key along step "B" to position "C", and the pusher 40 a corresponding length to dispense another implant. Multiple implants may be delivered in this fashion, with the number of implants delivered depending on the number of steps in the stepped slot.

Although the various implant delivery devices described above deploy solid implants, this invention also contemplates the use of the devices to deliver various semi-solid implants and gels into the sinus. A force applied to a predetermined amount of a semi-solid implant or gel composition in the conduit, e.g., by contact with a pusher or pressurized gas, could be used to deliver the implant or gel into the sinus.

Applications

The implants may be used to treat sinusitis affecting one or more of the maxillary sinus, the frontal sinus, the ethmoidal sinus, and the sphenoidal sinus.

Furthermore, the biodegradable implants may be used to treat acute or chronic sinusitis arising from predisposing anatomical conditions, chronic allergic processes, or conditions related to infection by various pathogens (e.g., bacteria, fungi, and viruses).

Examples of bacteria that may cause sinusitis include Alpha-hemolytic streptococci, Beta-hemolytic streptococci, *Branhamella catarrhalis,* Diptheroids, *Haemophilis influenzae, Moraxella* species, *Pseudomonas aeroginosa, Pseudomonas maltophilia, Serratia marcescens, Staphylococcus aureus,* and *Streptococcus pneumoniae.*

Examples of fungi that may cause sinusitis include Aspergillosis, *Candida, Cryptococcus, Coccidioides, Histoplasma,* and *Mucor* species.

The biodegradable implants may also be used to reduce inflammation resulting from a sinus procedure, typically, a sinus drainage procedure. Examples of sinus drainage procedures include, but are not limited to, widening/enlargement of a narrowed ostium, antral puncture and washout, and intranasal antrostomy. The implants may be delivered into a sinus using one of the methods previously described, usually after the procedure is completed, but they can also be delivered into a sinus before the procedure or during the procedure.

If enlarging an ostium, the affected sinus will generally be accessed through that enlarged ostium. The biodegradable implant(s) may then be deployed into the sinus via the enlarged ostium. With respect to antral puncture and drainage or intranasal antrostomy, the affected sinus usually will be accessed at the antral puncture site or through the antrostomy. The biodegradable implant(s) will also usually be deployed into the sinus through the antral puncture site or antrostomy. However, if desired, the biodegradable implant(s) may be delivered through a natural ostium despite antral puncture or antrostomy being perfomed.

Method of Making the Implants

The method of preparing the implants of this invention will generally depend on the particular therapeutic agent or matrix polymer used, form of the implant, and the release kinetics desired, but may be made by any one of the numerous methods known in the art. For example, the implants may be made by such processes as compression, extrusion, molding, solvent evaporation, or solvent extraction.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

The invention claimed is:

1. A method for delivering a drug-releasing implant into a paranasal sinus cavity comprising:
   a) loading a delivery device with one or more drug-releasing implants;
   b) creating access to the paranasal sinus cavity with the loaded delivery device such that at least a portion of the delivery device is advanced into the paranasal sinus cavity; and
   c) delivering the one or more drug-releasing implants from the delivery device-into the paranasal sinus cavity,
   wherein the one or more drug-releasing implants comprise a therapeutic amount of an active agent for the treatment of sinusitis.

2. The method of claim 1 wherein the one or more drug-releasing implants is a solid implant having a first delivery form for facilitating delivery into the sinus cavity and a second form, different from the first form, the second form having a shape that substantially prevents clearance of the implant from the sinus cavity.

3. The method of claim 1 wherein the one or more drug-releasing implants has a diameter of about 5 millimeters while in the conduit.

4. The method of claim 1 wherein delivering the one or more drug-releasing implants comprises delivering the one or more drug-releasing implants with a pusher.

5. The method of claim 1 wherein delivering the one or more drug-releasing implants comprises delivering the one or more drug-releasing implants with a pressurized gas.

6. The method of claim 1 wherein the one or more drug-releasing implants is a biodegradable polymeric implant.

7. The method of claim 1 wherein the delivery device Comprises a conduit.

8. The method of claim 1 wherein a distal portion of the delivery device is angulated.

9. The method of claim 8 wherein the distal portion of the delivery device is angulated at an angle between about zero degrees to about 135 degrees.

10. The method of claim 7 wherein the conduit comprises a distal opening at a tip of the conduit.

11. The method of claim 7 wherein the conduit comprises a distal opening in a side wall of the conduit.

12. The method of claim 1 wherein the one or more drug-releasing implants comprises a series of predetermined fracture lines.

13. The method of claim 1 wherein the one or more drug-releasing implants comprises a therapeutic amount of an anti-inflammatory active agent.

14. The method of claim 13 wherein the anti-inflammatory active agent comprises mometasone furoate.

15. The method of claim 13 wherein the anti-inflammatory active agent comprises budesonide.

16. The method of claim 13 wherein the anti-inflammatory active agent comprises fluticasone propionate.

17. The method of claim 13 wherein the anti-inflammatory active agent comprises triamcinolone acetonide.

18. The method of claim 1 wherein the one or more drug-releasing implants comprises a biodegradable matrix.

19. The method of claim 18 wherein the biodegradable matrix comprises a biodegradable polymer matrix.

20. The method of claim 19 wherein the biodegradable polymer matrix comprises a mucoadhesive polymer.

21. The method of claim 19 wherein the biodegradable polymer matrix comprises a poly(lactic-co-glycolic)acid (PLGA) copolymer.

22. The method of claim 19 wherein the biodegradable polymer matrix comprises lactic acid.

23. The method of claim 19 wherein the biodegradable polymer matrix comprises glycolic acid.

24. The method of claim 1 wherein the active agent is released over a treatment period of about one week to about three months.

25. The method of claim 1 wherein the active agent is released over a treatment period of about two weeks to about four weeks.

26. The method of claim 1 wherein the active agent is released over a treatment period of at least about one week.

27. The method of claim 1 wherein the active agent is released over a treatment period of at least about two weeks.

28. The method of claim 1 wherein the one or more drug-releasing implants comprises an active agent in an amount between about 5% and about 90% by weight of the one or more drug-releasing implants.

29. The method of claim 1 wherein the one or more drug-releasing implants is a rod, pellet, bead, strip, or microparticle.

30. The method of claim 1 wherein creating access to the paranasal sinus cavity comprises puncturing a sinus wall of the paranasal sinus.

31. A method for delivering a drug-releasing implant into a paranasal sinus cavity comprising:
   a) loading a delivery device with one or more drug-releasing implants;

b) creating access to the paranasal sinus cavity with the loaded delivery device such that at least a portion of the delivery device is advanced into the paranasal sinus cavity; and
c) delivering the one or more drug-releasing implants from the delivery device-into the paranasal sinus cavity,
wherein the one or more drug-releasing implants comprise a therapeutic amount of an active agent for the reduction of inflammation.

32. The method of claim 31 wherein creating access to the paranasal sinus cavity comprises puncturing a sinus wall of the paranasal sinus.

\* \* \* \* \*